US00PP15149P2

(12) United States Plant Patent
Vergara et al.

(10) Patent No.: US PP15,149 P2
(45) Date of Patent: Sep. 14, 2004

(54) LEUCOCORYNE PLANT NAMED 'ELENA'

(50) Latin Name: *Leucocoryne*
Varietal Denomination: Elena

(75) Inventors: Levi Mansur Vergara, Los Andes (CL); Gabriela Verdugo Ramirez, Quillota (CL)

(73) Assignee: Pontificia Universidad Catolica de Valparaiso, Valparaiso (CL)

( * ) Notice: Subject to any disclaimer, the term of this patent is extended or adjusted under 35 U.S.C. 154(b) by 0 days.

(21) Appl. No.: 10/455,334

(22) Filed: Jun. 6, 2003

(51) Int. Cl.[7] ..... A01H 5/00
(52) U.S. Cl. ..... Plt./263
(58) Field of Search ..... Plt./263

*Primary Examiner*—Kent Bell
(74) *Attorney, Agent, or Firm*—Foley & Lardner LLP

(57) ABSTRACT

A new and distinct cultivar of the Glory of the Sun plant named 'Elena' characterized by having: violet and white oblong tepals; staminodes with violet–blue apexes; and a large number of pedicels (5 to 12).

3 Drawing Sheets

Latin name of the genus and species of the plant claimed: Leucocoryne (species unknown).
Variety denomination: Elena.

BACKGROUND OF THE INVENTION

The present invention relates to a new and distinct cultivar of the Glory of the Sun plant, known in Chile as Huilli and botanically known as Leucocoryne. The new cultivar is referred to herein by the cultivar name 'Elena.' Leucocoryne are bulbous herbs that are native to Chile.

The new cultivar was selected from a population grown in a cultivated area (greenhouse) in, Chile in 1998, by the inventors, Levi Mansur Vergara and Gabriela Verdugo Ramirez. Asexual propagation has demonstrated that the combination of characteristics as herein disclosed for the new cultivar are firmly fixed and retained through successive generations of asexual reproduction. The new cultivar was first asexually reproduced in a cultivated area (greenhouse in Chile in 1999. The method used to asexually reproduce was natural bulbification. The new cultivar reproduces true-to-type.

BRIEF SUMMARY OF THE INVENTION

The following traits have been repeatedly observed and are determined to be basic characteristics of 'Elena' which in combination distinguish this Glory of the Sun as a new and distinct cultivar:

1. Number of Pedicels: 5–12.
2. Tepal shape: Oblong.
3. Tepal color: White base; violet apex, RHS N88 C; and
4. Staminode color: White base; violet-blue apex, RHS 93 B.

'Elena' has not been observed under all possible environmental conditions. The phenotype of the new cultivar, with the exception of flower design, as shown in the second drawing sheet, may vary with variations in environment such as temperature, light intensity, and day length without any change in the genotype of the plant. However, the phenotype is reproduced true-to-type under the environmental conditions in which they were observed. The following observations, measurements and values describe the new cultivar as grown in Quillota, Chile (32° 53' lat. S; 71° 16' long. W) under conditions that favor normal Leucocoryne growth.

BRIEF DESCRIPTION OF THE DRAWING

There are three accompanying drawings that illustrate the overall appearance of the new Glory of the Sun cultivar 'Elena'. These show the umbel, the flower, and the foliage of 'Elena'. The images portray colors as true as is reasonably possible with colored reproductions of this type.

The first photographic drawing shows the umbel of 'Elena', depicting a cluster of inflorescences and buds.

The second photographic drawing shows a close-up of the flower of 'Elena' and

The third photographic drawing shows the foliage of an adult plant of 'Elena'.

DETAILED BOTANICAL DESCRIPTION

The following observations, measurements and values describe the new cultivar as grown in Quillota, Chile (32° 53' lat. S; 71° 16' long. W) under conditions that favor normal Leucocoryne growth. The Glory of the Sun cultivar 'Elena' has been grown in unheated greenhouses from March to November, under a temperature regime as described in Table 1 below:

TABLE 1

Temperature data in Quillota, Chile (32° 53' lat. S; 71° 16' long. W)

| | Temperature Celsius | | | |
|---|---|---|---|---|
| Month | Maximum | Minimum | Minimum Absolute | Average |
| March | 25.6 | 9.8 | 5.30 | 17.70 |
| April | 27.7 | 8.1 | 3.60 | 15.40 |
| May | 19.9 | 7.4 | 2.70 | 13.65 |
| June | 16.9 | 5.8 | 0.90 | 11.35 |
| July | 16.8 | 5.5 | 0.40 | 11.15 |
| August | 18.2 | 5.8 | 0.10 | 12.00 |
| September | 19.7 | 6.9 | 2.40 | 13.30 |
| October | 21.9 | 8.2 | 3.30 | 15.05 |
| November | 24.7 | 9.1 | 5.20 | 16.90 |

Color references are made to The Royal Horticultural Society Colour Chart (R.H.S.) the Munsell Book of Colors, Munsell Color, Baltimore, Md. (1976), (Munsell), except where general colors of ordinary significance are used. Color values were taken under daylight conditions, approximately in September in Quillota. The plant characteristics described below are based on observations of adult plants capable of flowering with bulb weighing over 1.0 gram and grown in a container (diameter 20 cm; depth 20 cm).

Parentage:
- *Male parent.*—Leucocoryne (species unknown, unpatented).
- *Female parent.*—Leucocoryne (species unknown, unpatented).

Plant:
- *General appearance and form.*—Form: Geophytic herb. Height (typical): 68 cm. Height (range): 60–75 cm. Growth habit: Erect.

Foliage:
- *Overall shape of leaf.*—Linear.
- *Max length* (*typical*).—46 cm.
- *Max length* (*range*).—37–56 cm.
- *Width* (*typical*).—7.5 mm.
- *Width* (*range*).—5.0–11.0 mm.
- *Apex.*—Rounded.
- *Margin.*—Entire.
- *Color.*—Green–Yellow, Munsell Color Chart 5GY 7/8; 5GY 7/10 (both surfaces).

Scape:
- *Length* (*typical*).—60 cm.
- *Length* (*range*).—55–65 cm.
- *Diameter* (*typical*).—4.0 mm.
- *Diameter* (*range*).—3.5–4.5 mm.
- *Hardness.*—2 (on a scale of 1=soft, 2=hard, 3=very hard).
- *Color.*—Green–Yellow, Munsell Color Chart 5GY 6/10; 5GY 7/10.

Spathes:
- *Spathes per umbel.*—2.
- *Shape.*—Linear–Lanceolate.
- *Length* (*typical*).—4.4 cm.
- *Length* (*range*).—3.8–5.0 cm.

Umbels:
- *Depth* (*typical*).—9 cm.
- *Depth* (*range*).—8–10 cm.
- *Diameter* (*typical*).—14.5 cm.
- *Diameter* (*range*).—13–16 cm.
- *Number of flowers per umbel* (*typical*).—8.
- *Number of flowers per umbel* (*range*).—5–12.
- *Bulbils.*—None.

Pedicel:
- *Length* (*typical*).—4.6 cm.
- *Length* (*range*).—3.0–6.0 cm.

Flower:
- *Depth* (*typical*).—1.6 cm.
- *Depth* (*range*).—1.5–1.7 cm.
- *Diameter* (*typical*).—6.4 cm.
- *Diameter* (*range*).—5–7 cm.
- *Tepals per flower.*—6.
- *Aroma.*—None.
- *Lastingness of the bloom.*—10 weeks.

Tepal:
- *Shape.*—Oblong.
- *Apex.*—Lightly obtuse.
- *Base.*—Lightly acute.
- *Margin.*—Entire.
- *Length* (*typical*).—3.0 cm.
- *Length* (*range*).—2.9–3.1 cm.
- *Color of upper surface.*—White base (¼ of tepal), RHS 155 C; violet apex, RHS N88 C (¾ of tepal).
- *Color of lower surface.*—White base (¼ of tepal), RHS 155 C; violet apex, RHS N88 C (¾ of tepal).

Bulb:
- *Shape.*—Globular, somewhat flattened basally.
- *Diameter.*—Typical Equatorial Diameter of Adult Bulb: 2.0–3.0 cm. Maximum Equatorial Observed: 4.9 cm.
- *Weight.*—Typical fresh weight of adult bulb: 4.0–15.0 gr. Maximum fresh weight of adult bulb: 24.0 gr.
- *Skin color.*—Greyed–orange, RHS N163 A; 167 A; 167 B.
- *Dropper per bulb.*—0–3.

Dropper: (Stolon-like structure that grows from the bulb and produce a bulb at the tip).
- *Diameter equatorial.*—1.0–1.4 cm.
- *Weight.*—0.9–1.7 gr.
- *Dropper shape.*—Ovate (elongated-oval).
- *Dropper skin color.*—Greyed–orange, RHS N163 A; 167 A; 167 B.

Reproductive organs:
- *Anthers.*—Quantity: 3. Size: 3 mm. Color: Yellow, Munsell Color Chart 5Y 8/12.
- *Staminodes.*—Quantity: 3. Size: 6.5–8.0 mm. Color: White base (¾ of staminode); violet–blue apex, RHS 93 B (¼ of staminode).
- *Pistils.*—1 per flower.
- *Stigma and styles.*—Style short and cylindrical; stigma somewhat capitate.
- *Ovaries.*—Quantity: 1. Size: 4.5–5.0 mm. Color: Green–Yellow (Munsell Color Chart 7.5GY 4/6; 7.5GY 5/8; 7.5GY 7/8; 7.5GY 8/8).
- *Pollen.*—Viable.
- *Seed.*—Viable. Amount (typical): 7 per fruit. Amount (range): 0–15 per fruit. Size: 1.5 mm. Color: Black RHS 202 A.

Disease resistance/susceptibility: No information to date.

Pest resistance/susceptibility: Susceptible to *Pseudococcus affinis.*

We claim:

1. A new and distinct cultivar of the Glory of the Sun plant named 'Elena', substantially as illustrated and described herein.

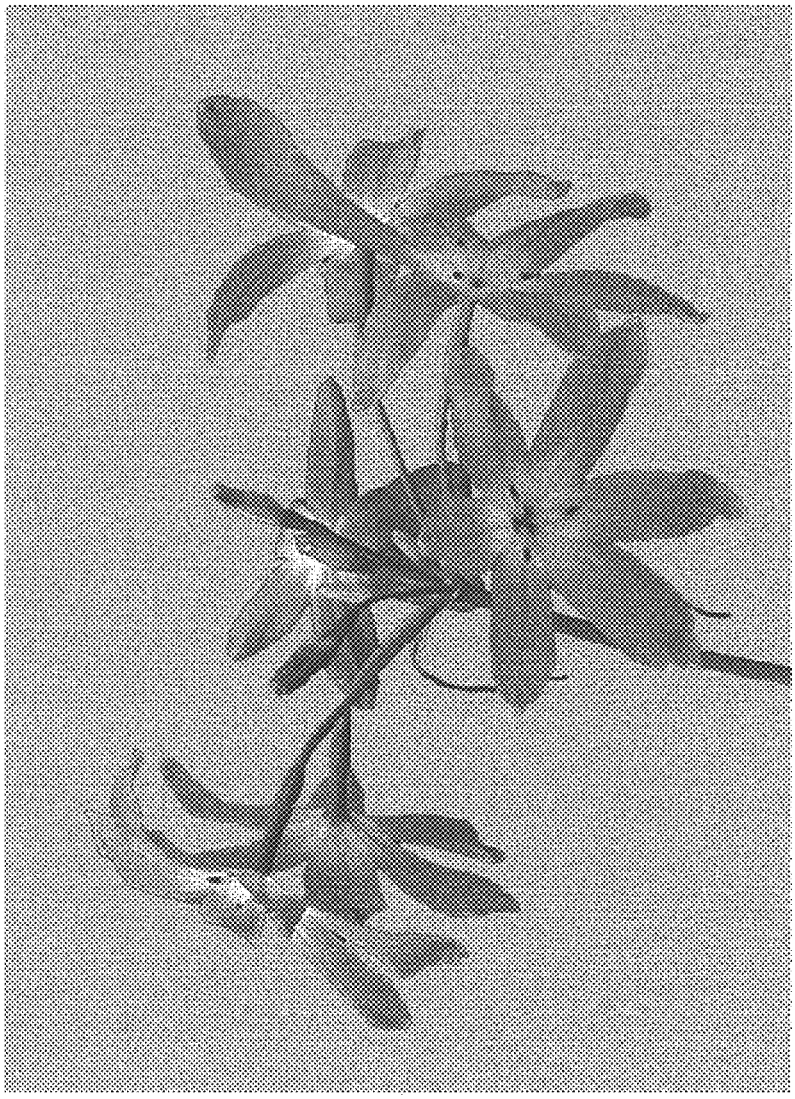

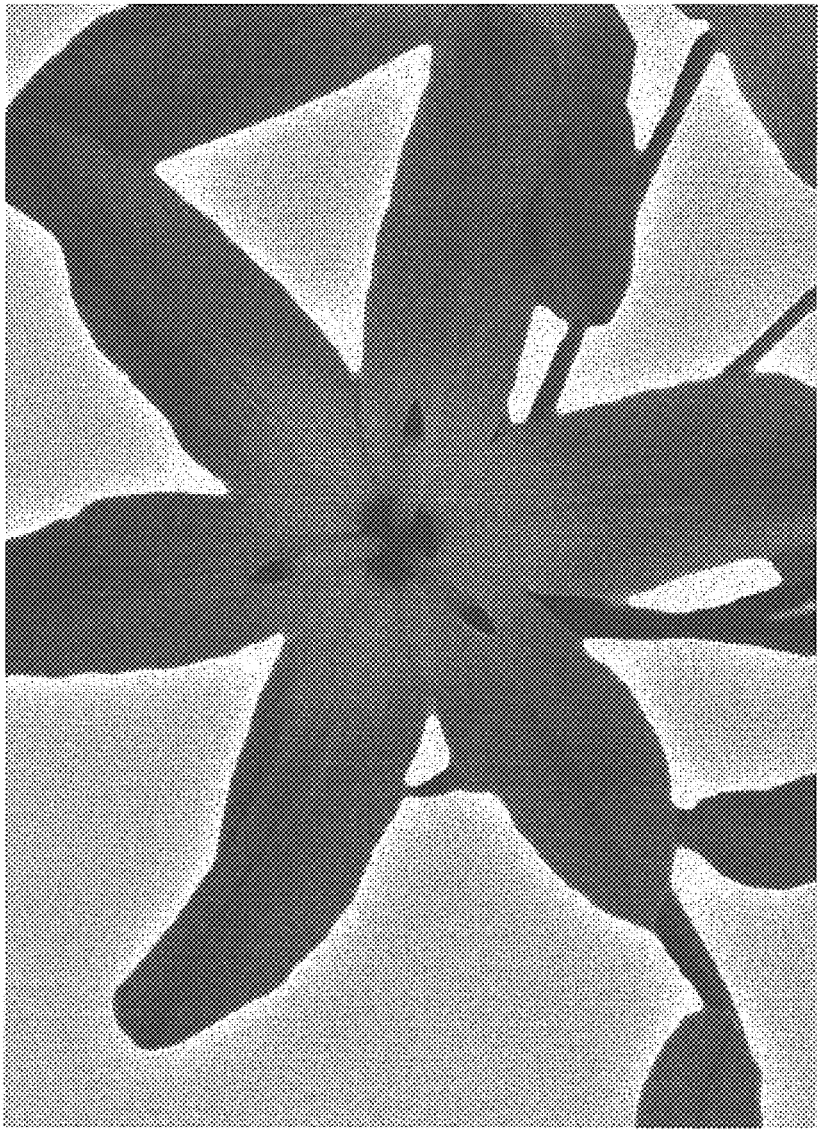

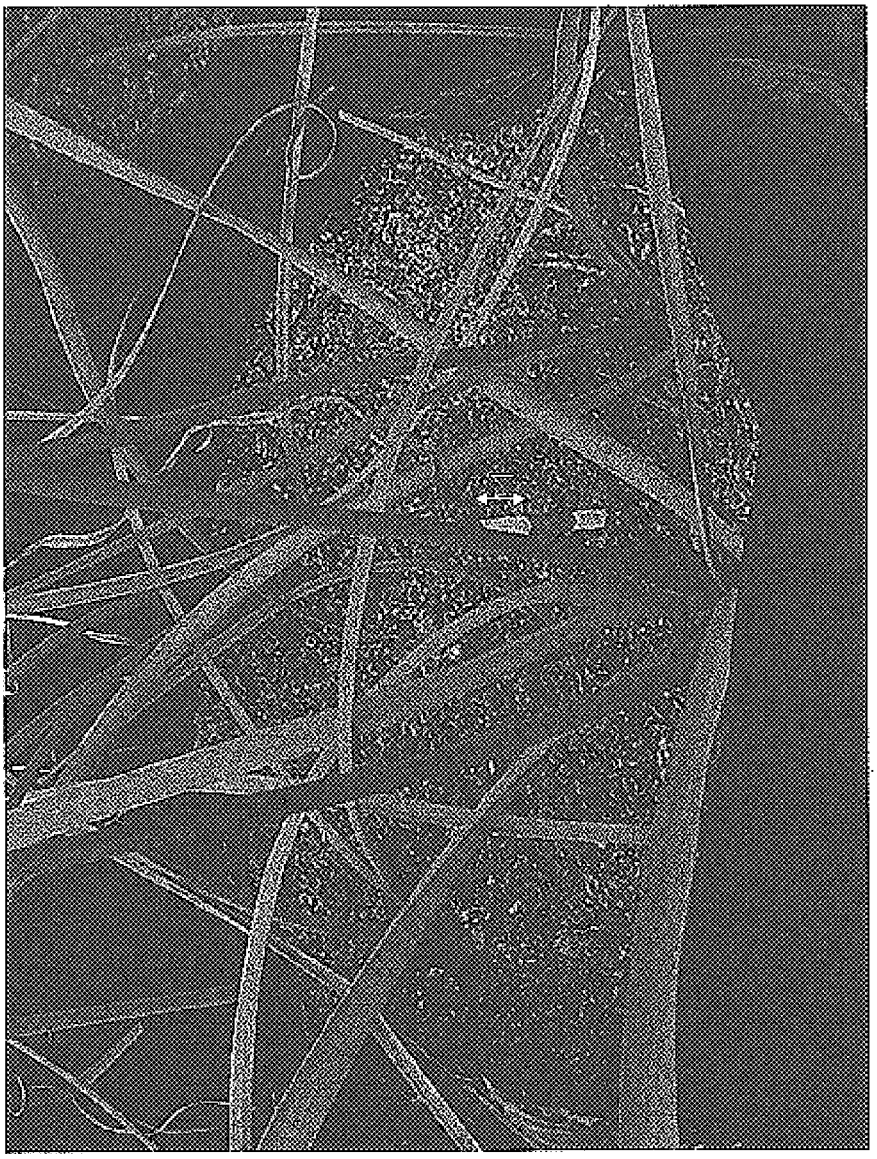

* * * * *